US007115117B2

(12) United States Patent
Shiraishi et al.

(10) Patent No.: US 7,115,117 B2
(45) Date of Patent: Oct. 3, 2006

(54) INFUSION VESSEL

(75) Inventors: Yasuyuki Shiraishi, Urayasu (JP); Keiji Hamamoto, Osaka (JP); Seiji Yoshimura, Ibaraki (JP)

(73) Assignee: Taisei Kako Co., Ltd., (JP)

(*) Notice: Subject to any disclaimer, the term of this patent is extended or adjusted under 35 U.S.C. 154(b) by 310 days.

(21) Appl. No.: 10/370,266

(22) Filed: Feb. 19, 2003

(65) Prior Publication Data

US 2003/0158537 A1 Aug. 21, 2003

(30) Foreign Application Priority Data

Feb. 21, 2002 (JP) ............................ 2002-045312

(51) Int. Cl.
*A61B 19/00* (2006.01)
*B65D 25/08* (2006.01)
*B65D 1/24* (2006.01)
*A61J 1/00* (2006.01)

(52) U.S. Cl. ...................... 604/416; 206/219; 220/501; 220/529

(58) Field of Classification Search ................ 604/403, 604/411, 415, 416, 533–535, 905; 206/363–366, 206/219, 221; 222/129; 215/DIG. 8, DIG. 3; 220/23.86, 501, 529
See application file for complete search history.

(56) References Cited

U.S. PATENT DOCUMENTS 4,727,985 A * 3/1988 McNeirney et al. ........ 206/221
4,871,354 A 10/1989 Conn et al.
4,903,865 A * 2/1990 Janowitz .................... 222/83.5
5,291,991 A * 3/1994 Meyer ...................... 206/221
5,509,530 A * 4/1996 Wilson ...................... 206/220
5,875,889 A * 3/1999 Albisetti .................... 206/221

FOREIGN PATENT DOCUMENTS

JP 10243990 A 9/1998

* cited by examiner

*Primary Examiner*—Patricia Bianco
*Assistant Examiner*—Leslie R. Deak
(74) *Attorney, Agent, or Firm*—Wood, Phillips, Katz, Clark & Mortimer

(57) ABSTRACT

The present invention provides an infusion vessel, which is capable of separately containing a drug and a infusion liquid in a sterile manner and mixing the drug with the infusion liquid in a sterile manner by a simple operation for use, while ensuring the sterility of a connector thereof. The infusion vessel according to the present invention comprises a bag (2) for containing a infusion liquid, a two-mouth vial (3) for containing a drug, and a joint (4) connecting the bag and the vial. A lower mouth portion (33) of the vial (3) is sealed with a rubber plug (7). The joint (4) is air-tightly connected to a liquid outlet port (21) provided in a bottom portion of the bag (2), and extends downward. The joint (4) has an opening (46) for communication between the inside and the outside thereof. An O-ring (6) and an intermediate rubber plug (5) are respectively attached to the joint (4) above and below the opening (46), and fitted in the upper mouth portion (32) of the vial (3) in an axially movable manner.

17 Claims, 7 Drawing Sheets

INFUSION VESSEL

BACKGROUND OF THE INVENTION

1. Field of the Invention

The present invention relates to an infusion vessel which is capable of separately containing a drug and a infusion liquid in a sterile manner, and mixing the drug with the infusion liquid in a sterile manner by a simple operation for use.

2. Description of Related Art

Conventional infusion vessels of on-demand dissolution type are disclosed, for example, in Japanese Unexamined Patent Publications No. 5-103820 (1993), No. 2-1277 (1990) and No. 60-132561 (1985).

In an infusion vessel disclosed in Japanese Unexamined patent Publication No. 5-103820 (1993), a drug container and a diluent container (liquid container) are independently provided and, as required, are connected in communication with each other. The drug container has a diluent communication port and a drug solution outlet port provided on opposite sides thereof, and seal members are respectively attached to these ports. The diluent container has a connector attachable to the diluent communication port of the drug container. When the infusion vessel is used, caps of the drug container and the diluent container independently provided as shown in FIGS. 2 and 3 in this patent publication are removed, and the drug container and the diluent container are connected to each other. The diluent container is sterilized by means of an autoclave and a drug is filled in the drug container in a sterile room, whereby the insides of the diluent container and the drug container are kept sterile. However, when the drug container and the diluent container are connected to each other for use, the connector and communication means such as a needle are exposed to the atmosphere, so that the connector is liable to be contaminated with bacteria and viruses in the atmosphere. As a result, it is impossible to ensure the sterility of the infusion liquid.

An infusion vessel disclosed in Japanese Unexamined Patent Publication No. 2-1277 (1990) includes a infusion liquid bag (flexible container), a resin capsule connected to an upper portion of the infusion liquid bag via a liquid channel, and a glass vial retained in the capsule. A fracturable rubber plug seals the liquid channel, and a rubber plug also seals a mouth of the vial. A two-tip needle is provided in the liquid channel. For use, the rubber plugs of the vial and the liquid channel are pierced with the needle by pressing down the vial, so that the inside of the vial communicates with the inside of the bag. In order to ensure the sterility of the infusion vessel having such a construction even after the communication is established between the vial and the bag, the two-tip needle and a space between the vial and the capsule should also be kept sterile. After the assembling of the infusion vessel, the space between the vial and the capsule can be sterilized by steam penetrating through the capsule in an autoclave sterilization process. However, the steam is condensed on an interior surface of the capsule after the autoclave process, so that water droplets remain in the capsule. This impairs the product value. Further, it is impossible to employ EO sterilization and electron beam sterilization from the viewpoint of the stability of the drug. Therefore, the entire production process from the filling of a infusion liquid to the assembling should be performed in a sterile atmosphere.

An infusion vessel disclosed in Japanese Unexamined Patent Publication No. 60-132561 (1985) includes a infusion liquid bag having a cylindrical top opening, a plastic sleeve fixed to the cylindrical top opening of the bag by heat-sealing, and a glass sleeve fitted in the plastic sleeve, and is adapted to contain a drug in the glass sleeve. Two rubber plugs are fitted in the glass sleeve, and the drug is contained in a space defined between the rubber plugs. In order to ensure the sterility of the inside of the bag of the infusion vessel having such a construction, it is essential to thoroughly inspect a circumferential portion of the top opening of the bag heat-sealed to the plastic sleeve to check the integrity of the heat seal. This increases quality control costs.

SUMMARY OF THE INVENTION

In view of the various problems associated with the conventional infusion vessels described above, it is an object of the present invention to provide an infusion vessel of a novel construction, which is capable of easily separately containing a drug and a infusion liquid in a sterile manner and mixing the drug with the infusion liquid in a sterile manner by a simple operation for use, while ensuring the sterility of a connector thereof.

The infusion vessel according to the present invention comprises a vessel body having an inside space serving as a infusion liquid containing portion, a two-mouth vial having an inside space serving as a drug containing portion, a joint connecting the vessel body and the vial, first and second airtight members attached to the joint, and a third airtight member attached to the vial. The vessel body has a liquid outlet port provided in a bottom portion thereof. It is noted that vertical expressions are herein used for convenience of defining positional relationships of the respective components and, for example, a case where the liquid outlet port is located on the upper side of the vessel body in actual use is also covered by the present invention.

The vial may has upper and lower cylindrical mouth portions, and a body provided between the upper and lower mouth portions and having a greater diameter than the mouth portions. The mouth portions may be formed integrally with the body, or formed as separate members and fixed to opposite sides of the body thereby to be united with the body. The body of the vial has a diameter progressively increasing toward a lower side thereof from the upper mouth portion. The mouth portions have a vertical axis. The lower mouth portion is air-tightly sealed with the third airtight member. The vial may be composed of a material impermeable to steam, for example, a glass.

The joint has a proximal portion air-tightly connected to a peripheral edge of the liquid outlet port of the vessel body, and a cylindrical connector extending downward from the proximal portion. The connector has an opening for communication between the inside and the outside thereof.

The first airtight member is attached to the joint below the opening, and fitted in the upper mouth portion of the vial in an axially slidable manner so as to air-tightly close the upper mouth portion of the vial.

The second airtight member is attached to the joint above the opening, and fitted in the upper mouth portion of the vial in an axially slidable manner so as to seal a space defined between the connector and the upper mouth portion of the vial.

By moving the vial upward with respect to the joint, the first airtight member is disengaged downward from the upper mouth portion of the vial (e.g., inwardly of the vial), so that the inside space of the vessel body communicates with the inside space of the vial via the opening of the connector.

The infusion vessel according to the present invention is assembled while portions of the infusion vessel to be brought into contact with a infusion liquid (e.g., an interior surface of the vessel body, interior surfaces of the proximal portion and the connector of the joint, an interior surface of the vial, an exterior surface of the first airtight member, and the like) are kept sterile. Since the proximal portion of the joint and the liquid outlet port of the vessel body are air-tightly connected to each other after the assembling, there is no possibility that bacteria and viruses intrude into the container from the connector. The third airtight member air-tightly closes the lower mouth portion of the vial and, hence, there is no possibility that bacteria and viruses intrude into the vial from the lower mouth portion. Further, the opening of the connector is located below the second airtight member fitted in the upper mouth portion of the vial (inside the vial), so that an inside space of the connector is kept hermetic with respect to the atmosphere by the second airtight member. Thus, there is no possibility that bacteria and viruses intrude into the connector. Just before instillation is started, the vial is moved upward with respect to the joint to establish communication between the inside space of the vessel body and the inside space of the vial via the opening of the connector. Thus, a drug in the vial is mixed with the infusion liquid in the vessel body.

According to the present invention, all the portions of the infusion vessel to be brought into contact with the infusion liquid can easily be kept sterile when the drug is mixed with the infusion liquid for use. Since the infusion liquid is not brought into contact with exterior surfaces of the vial and the joint, there is no need for ensuring the sterility of the exterior surfaces. The portions of the infusion vessel to be brought into contact with the infusion liquid can be kept sterile by performing a drug filling operation, a infusion liquid filling operation and an assembling operation in a sterile room and properly performing sterilization processes such as autoclave sterilization after the assembling operation. Since the infusion vessel is not designed so that a rubber plug and a diaphragm are pierced with a needle, there is no possibility that the infusion liquid is contaminated with rubber scum or the like resulting from the piercing.

The infusion vessel according to the present invention may further comprise a stopper removably provided for prevention of axial movement of the vial with respect to the joint. Thus, the stopper prevents the vial from being inadvertently moved with respect to the joint during storage or transportation of the infusion vessel before use.

Instead of the stopper, an engagement member (engagement projection) may be provided for positioning the vial in a squeezed state and in a non-squeezed state. With this arrangement, the engagement member initially positions the vial in the non-squeezed state in engagement with the joint. By applying a force for disengagement of the engagement member, the vial is squeezed toward the joint. When the vial is completely squeezed toward the joint, the engagement member positions the vial in the squeezed state in engagement with the joint. This prevents the inadvertent movement of the vial.

The infusion vessel may further comprise restriction means for preventing the second airtight member from being disengaged downward from the upper mouth portion of the vial. With this arrangement, the intrusion of bacteria and viruses into the vial from the upper mouth portion can be prevented, which may otherwise occur due to the disengagement of the second airtight member from the upper mouth portion. The restriction means may be configured in any of various ways. For example, the restriction means may be configured such that an upper edge of the upper mouth portion of the vial abuts against the joint from a lower side with the first airtight member disengaged downward from the upper mouth portion and with the second airtight member fitted in the upper mouth portion. Alternatively, the restriction means may comprise engagement members respectively provided on a holder and a sleeve (to be described later) for restricting relative rotation of the holder and the sleeve in a vial squeezing direction with the first airtight member disengaged downward from the upper mouth portion and with the second airtight member fitted in the upper mouth portion.

The infusion vessel according to the present invention may further comprise a cylindrical holder for holding the vial, and a sleeve attached to the joint. The holder may be configured so as to cover the body of the vial, or to hold the upper mouth portion of the vial with the body of the vial exposed. The sleeve may be formed integrally with the joint, or formed separately from the joint and attached to the joint. The holder and the sleeve may threadingly be engaged with each other, so that the vial is axially moved with respect to the joint by moving the holder in threading engagement with the sleeve. Even where sufficient fitting margins are provided for ensuring the airtightness of the first and second airtight members, the mixing operation can assuredly be performed on demand for use by gradually axially squeezing the vial toward the joint by the relative rotation of the holder and the sleeve with application of a relatively small force. Since the axial movement of the vial is permitted only by the relative rotation of the holder and the sleeve, this arrangement is effective for preventing the inadvertent squeezing of the vial.

The holder may be composed of a transparent or translucent resin material. Thus, the vial and the joint can visually be inspected through the holder.

The vessel body may comprise a flexible bag of a resin material. The joint may be composed of a resin material compatible with the resin material for the vessel body. Thus, the proximal portion of the joint can easily and assuredly be connected to the liquid outlet port in an airtight manner by a fusion-bonding method such as ultrasonic fusion bonding. Examples of the material for the vessel body include vinyl chloride resin materials and polyolefin resin materials. Among the polyolefin resin materials, polyethylene resin materials and polypropylene resin materials are preferred because they are excellent in chemical resistance with little elution into the infusion liquid. Similarly, vinyl chloride resin materials and polyolefin resin materials are usable as the material for the joint.

The first airtight member is attached to a lower end of the connector of the joint. Further, the first airtight member has a cross section covering the entire inside space of the upper mouth portion of the vial. Thus, the upper mouth portion of the vial can assuredly be sealed, thereby eliminating a possibility that steam resulting from evaporation of the infusion liquid in the vessel body intrudes into the vial through the joint.

The first, second and third airtight members are preferably each composed of a rubber, particularly a butyl rubber. With this arrangement, the respective airtight members are impermeable to steam and oxygen. Thus, the intrusion of steam and oxygen into the vial can assuredly be prevented, so that the drug in the vial can be kept stable.

It is particularly preferred that the vial is composed of a glass. Where a drug having efficacy stability data obtained by employing an ordinary glass vial is used in the inventive infusion vessel, it is possible to utilize the efficacy stability data. Where an existing drug is used, the drug can be freeze-dried in the vial of the infusion vessel in a freeze-dryer. Therefore, it is merely necessary to partly modify a production system. Where the infusion liquid in the vessel body is sterilized by means of an autoclave after attaching the vial to the vessel body via the joint assembles the infusion vessel, the drug can be kept stable with no possibility that steam intrudes into the vial.

The infusion liquid in the vessel body, the drug in the vial, the interior surfaces of the proximal portion and the connector of the joint, the lower surface of the first airtight member and the interior surface of the upper mouth portion of the vial ranging from a portion thereof adjacent to the opening of the connector of the joint to the drug containing portion in the inventive infusion vessel are preferably kept sterile. More preferably, the interior surface of the vessel body, the interior surface of the vial, the interior surface of the joint, a junction between the joint and the first airtight member, the portion adjacent to the opening of the connector of the joint, the entire surface of the first airtight member, a portion (including the interior surface) of the third airtight member engaged with the vial and the lower surface of the second airtight member are all kept sterile. The term "sterile" herein means that the respective portions of the components of interest are not exposed to the atmosphere after sterilization thereof.

In the infusion vessel according to the present invention, the third airtight member attached to the lower mouth portion of the vial may be a rubber plug to be pierced with an instillation needle. Thus, the rubber plug is pierced with the needle connected to an instillation tube for instillation, while ensuring the airtightness of the lower mouth portion.

PREFERRED EMBODIMENT OF THE PRESENT INVENTION

With reference to the attached drawings, the present invention will hereinafter be described by way of an embodiment thereof.

Figure 1:
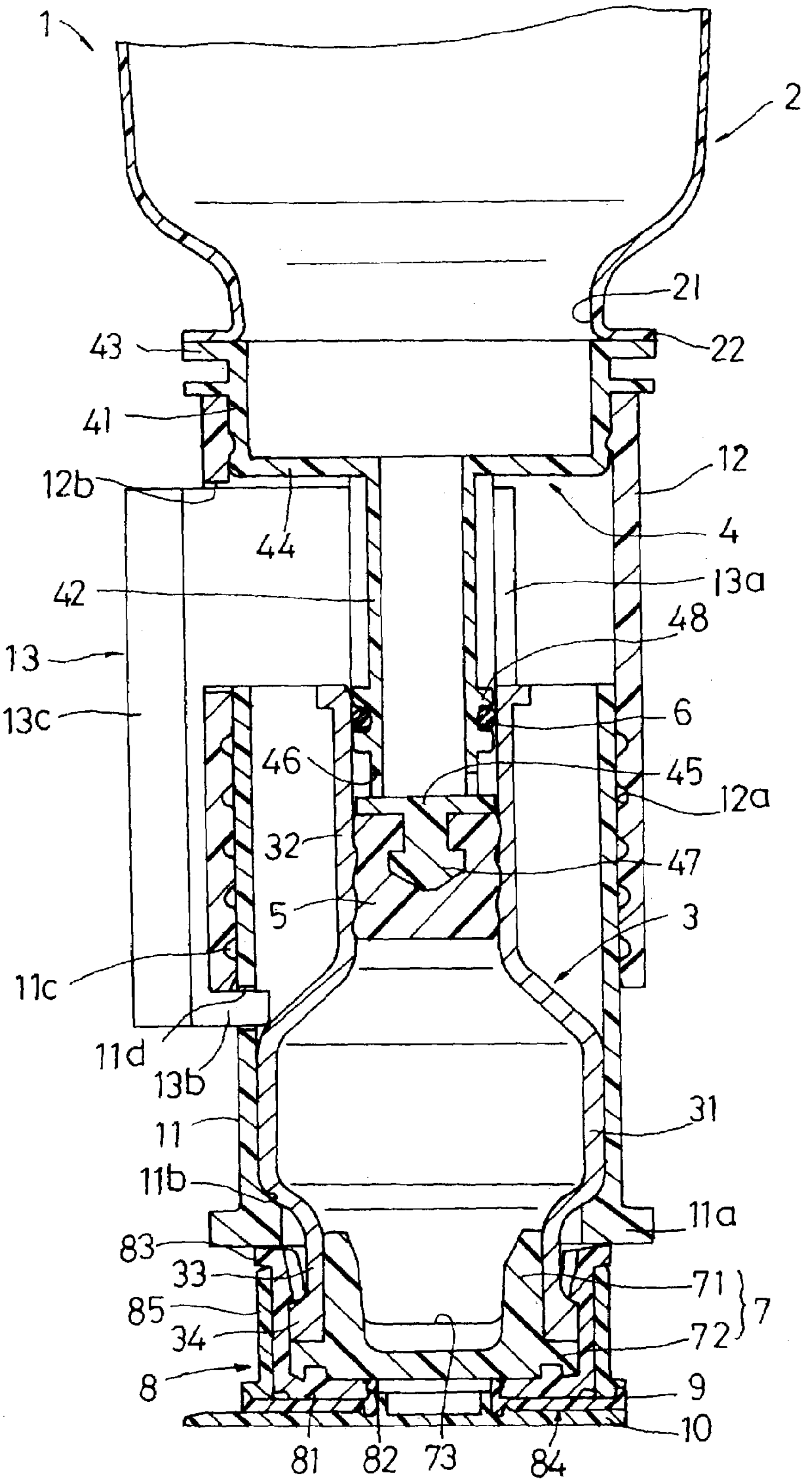
FIG. 1 is a vertical sectional view of an infusion vessel according to one embodiment of the present invention.
Figure 2:
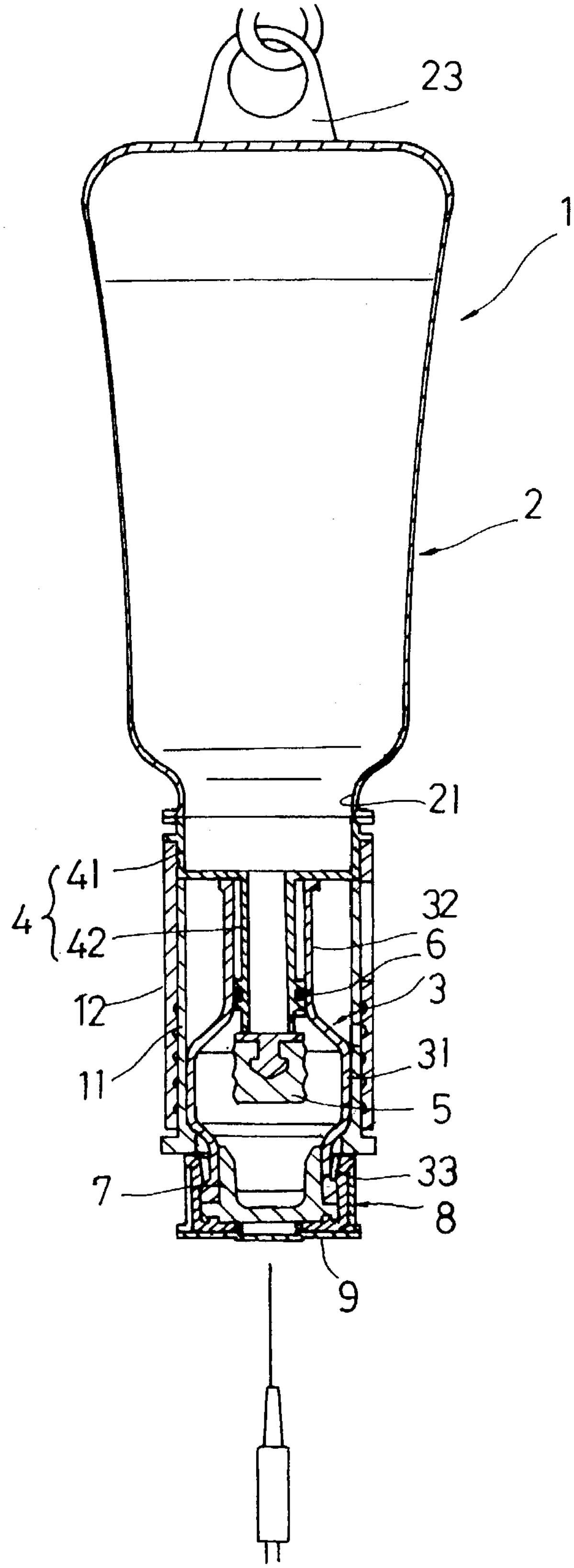
FIG. 2 is an enlarged vertical sectional view of major portions of the infusion vessel.
Figure 3:
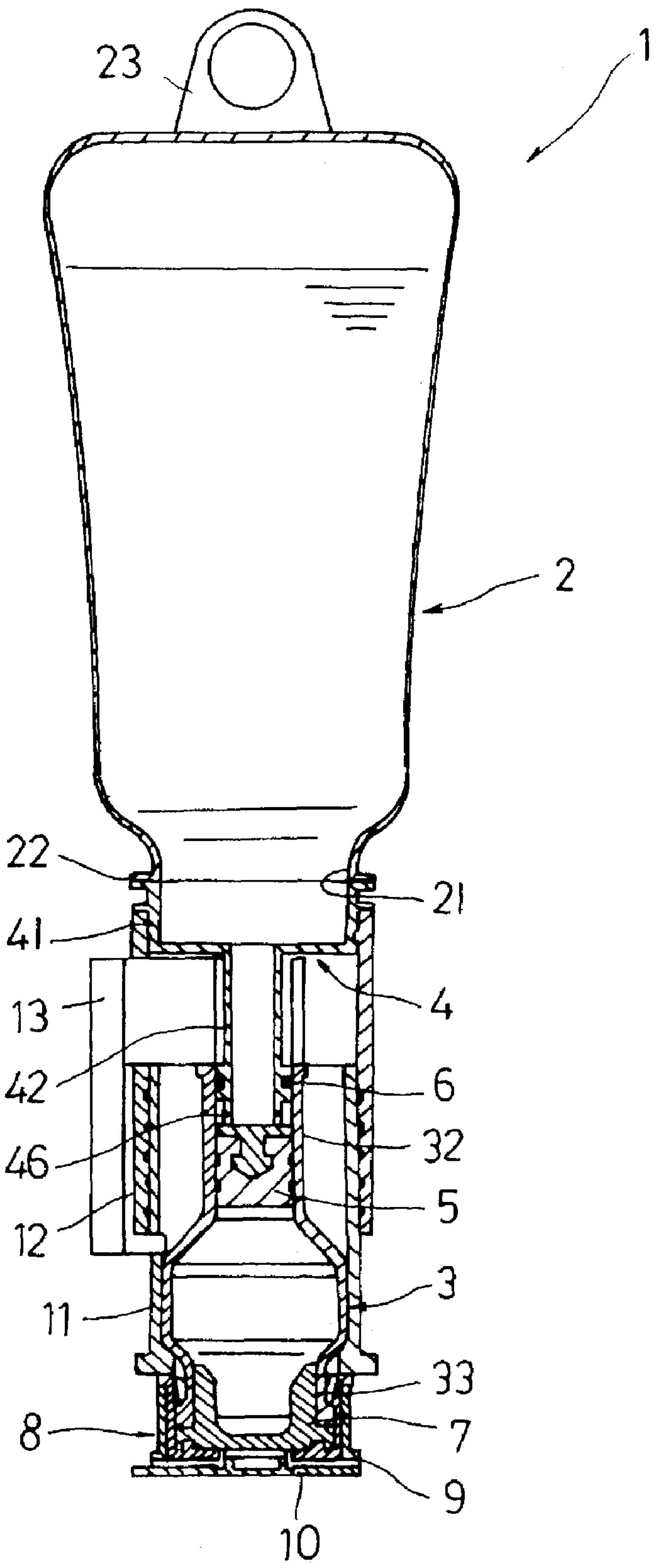
FIG. 3 is a vertical sectional view of the infusion vessel in a state where an inside space of a vessel body communicates with an inside space of a vial when the vial is squeezed into a sleeve by rotating a holder with respect to the sleeve with a stopper removed.
Figure 4:
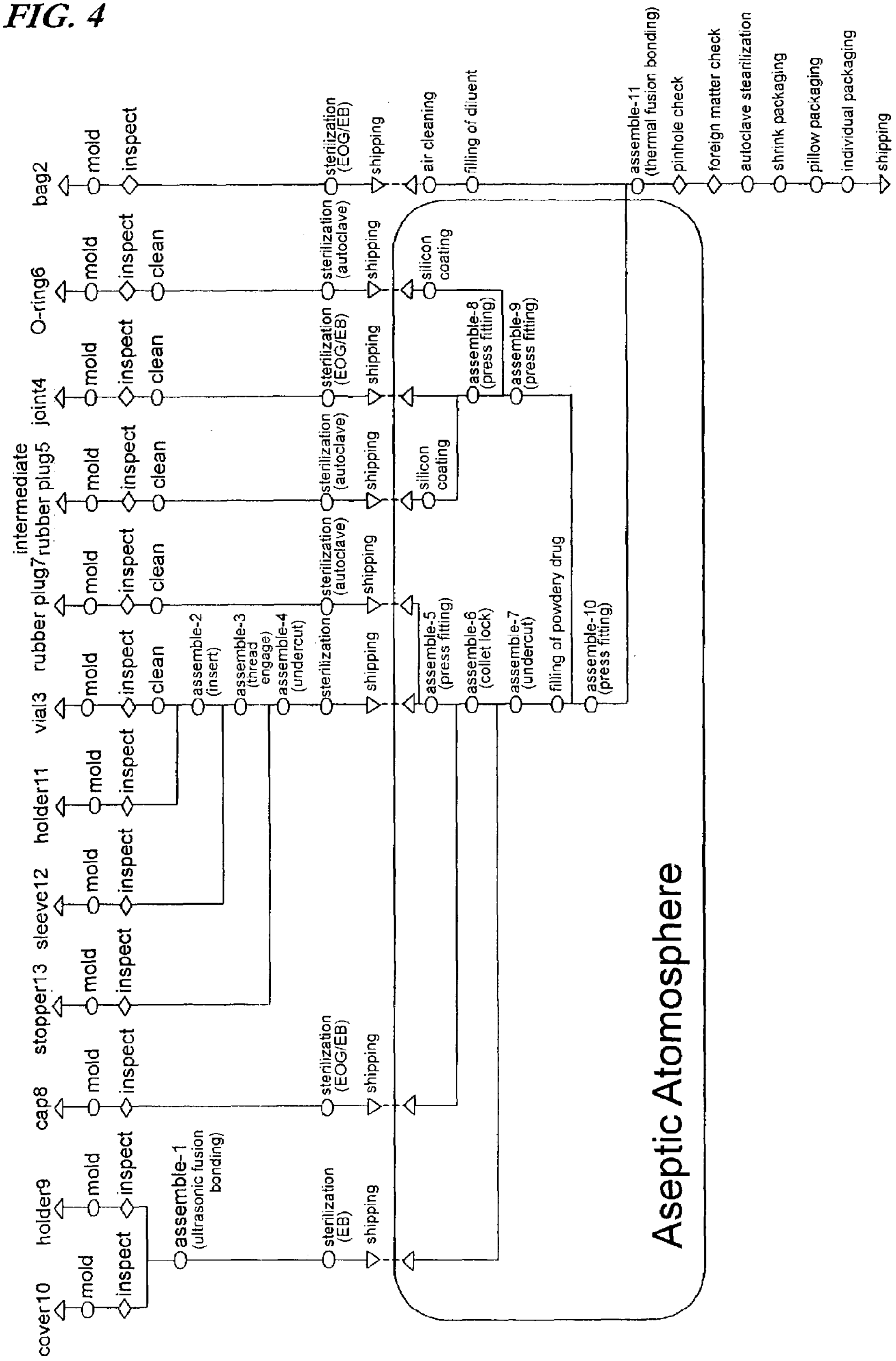
FIG. 4 is a process diagram illustrating an exemplary assembling process for the infusion vessel.
Figure 5:
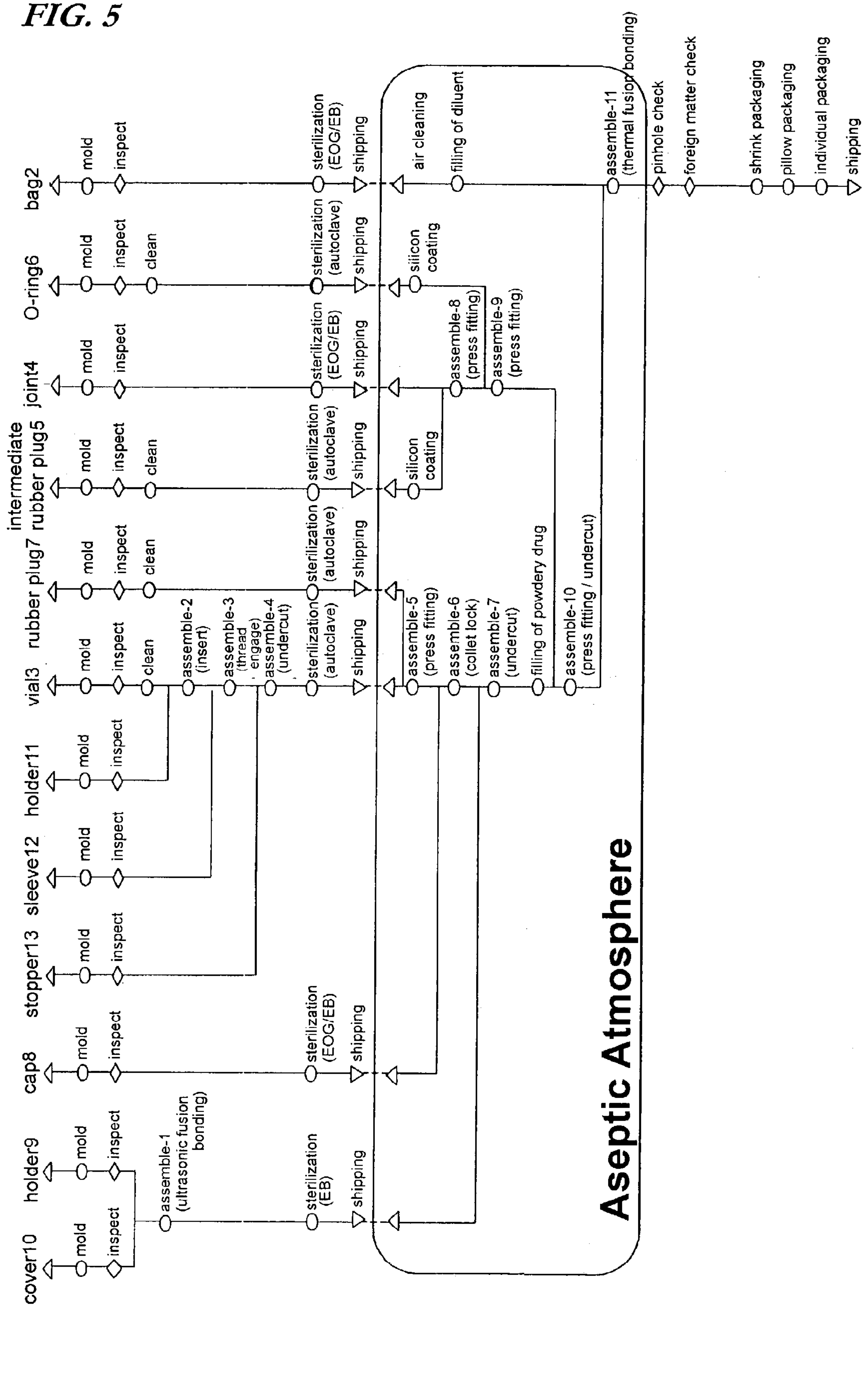
FIG. 5 is a process diagram illustrating another exemplary assembling process for the infusion vessel.
Figure 6:
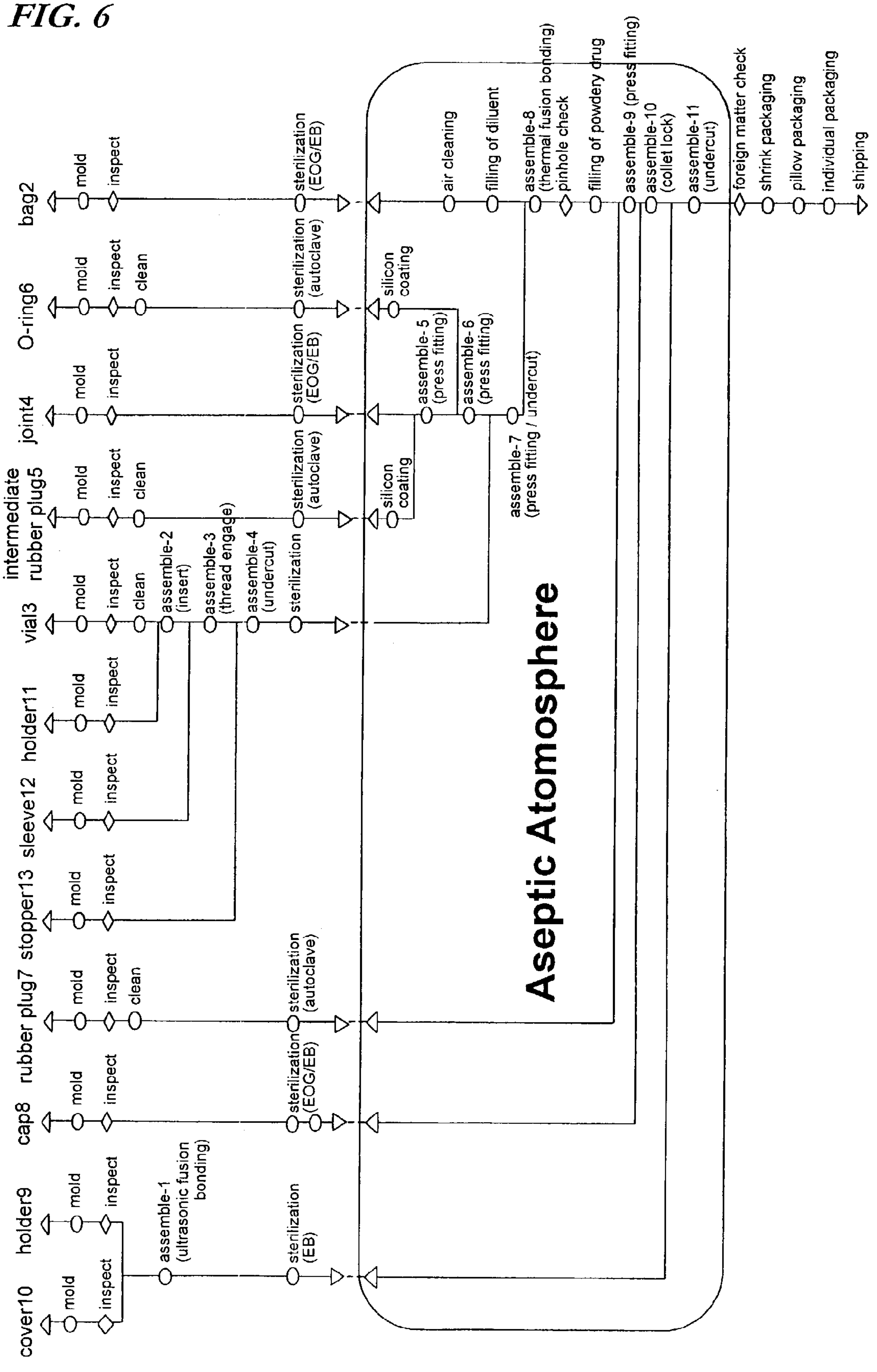
FIG. 6 is a process diagram illustrating further another exemplary assembling process for the infusion vessel.
Figure 7:
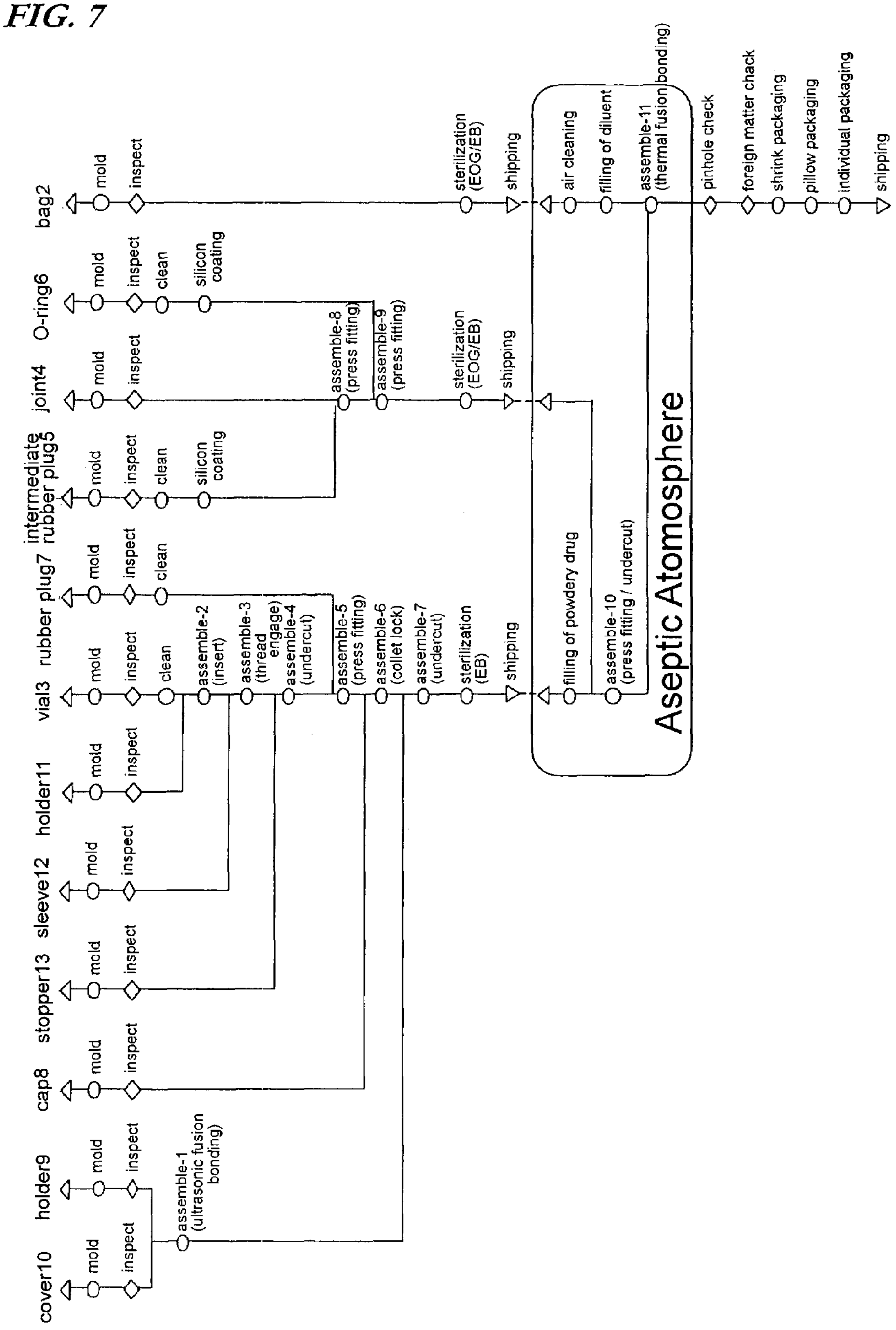
FIG. 7 is a process diagram illustrating still another exemplary assembling process for the infusion vessel.

FIGS. 1 to 3 illustrate an infusion vessel 1 according to the embodiment of the present invention. The infusion vessel 1 includes a flexible resin bag (vessel body) 2 having an inside space serving as a infusion liquid containing portion, and a two-mouth vial 3 connected to a lower portion of the bag 2 via a joint 4 and having an inside space serving as a drug containing portion. A infusion liquid to be contained in the bag 2 may be any of various types of liquids to be employed for dissolution, dispersion or dilution of a drug. Specific examples of the infusion liquid include physiological saline, a glucose solution, a Ringer's solution, distilled water for injection and an amino acid infusion solution. Examples of a drug to be contained in the vial 3 include antibiotic agents, antitumer agents and antiulcer agents.

The bag 2 has an open bottom serving as a liquid outlet port 21. The bag 2 has a flange 22 extending radially outwardly from a lower peripheral edge of the liquid outlet port 21. A hanger tab 23 having a hanger hole is provided on an upper portion of the bag 2 for hanging the infusion vessel 1. Although the flexible bag 2 is employed as the vessel body in this embodiment, a hard bottle may be employed.

The joint 4 has a cylindrical proximal portion 41 air-tightly connected to the peripheral flange 22 around the liquid outlet port 21 of the bag 2 by fusion bonding, and a cylindrical connector 42 extending downward from the proximal portion 41. A flange 43 is provided along an upper peripheral edge of the proximal portion 41 in opposed relation to the flange 22 of the bag 2. These flanges 22 and 43 are fusion-bonded with each other along the entire circumference thereof by a proper method such as thermal fusion bonding or ultrasonic fusion bonding. The proximal portion 41 has a bottom plate 44 provided at a lower end thereof. The connector 42 is connected to an axial center portion of the bottom plate 44. The connector 42 has a predefined axial length, and a distal end (lower end) thereof is closed by a closure (bottom plate) 45. The connector 42 has an opening 46 formed in a peripheral wall thereof above the closure 45 for communication between the inside and the outside of the connector 42. A projection 47 is provided on a distal end face of the connector 42 (i.e., a lower surface of the closure 45) as projecting downward. An intermediate rubber plug (first airtight member) 5 is attached to the projection 47, and fitted in an upper mouth portion of the vial 3. An O-ring receiving portion 48 is provided on an outer peripheral surface of the connector 42 above the opening 46, and an O-ring (second airtight member) 6 is fitted in the O-ring receiving portion 48.

The vial 3 is a glass bottle having a body 31 and upper and lower cylindrical mouth portions 32, 33 provided integrally with the body 31. The upper and lower mouth portions 32, 33 have a vertical axis. The upper mouth portion 32 has an axial length corresponding to the axial length of the connector 42. The inner diameter of the upper mouth portion 32 is uniform along the entire axial length, and is greater than the outer diameter of the connector 42 of the joint 4. The body 31 has a diameter greater than the diameters of the upper and lower mouth portions 32, 33. That is, an inner peripheral surface of the body 31 is connected to a lower edge of an inner peripheral surface of the upper mouth portion 32, and the body 31 has an inner diameter progressively increasing toward the lower side thereof. A lower portion of the body 31 has a diameter progressively decreasing toward the lower mouth portion 33 so as to be connected to the lower mouth portion 33. In this embodiment, the diameter of the lower mouth portion 33 is slightly greater than the upper mouth portion 32.

Before the drug is mixed with the infusion liquid for use, the distal opening 46 of the connector 42 of the joint 4 is located in an axially middle portion of the upper mouth portion 32 of the vial 3. A space defined between the outer peripheral surface of the connector 42 and the inner peripheral surface of the upper mouth portion 32 is air-tightly sealed by the O-ring 6 attached to the joint 4 above the opening 46, and the upper mouth portion 32 of the vial 3 is air-tightly closed by the intermediate rubber plug 5 attached to the joint 4 below the opening 46. The intermediate rubber plug 5 and the O-ring 6 are air-tightly fitted in the upper mouth portion 32 in an axially slidable manner.

Therefore, when the vial 3 is moved upward with respect to the joint 4, the intermediate rubber plug 5 is disengaged downward from the upper mouth portion 32 of the vial 3. Thus, the inside space of the bag 2 communicates with the inside space of the vial 3 via an internal channel of the connector 42 and the opening 46.

A distal rubber plug (third airtight member) 7 is attached to the lower mouth portion 33 of the vial 3. The rubber plug 7 is air-tightly fitted in the lower mouth portion 33. The rubber plug 7 includes an airtight plug portion 71 and a flange 72 integrally formed with the airtight plug portion 71. The airtight plug portion 71 is fitted in the mouth portion 33, and the flange 72 is in contact with a lower end face of the mouth portion 33. The flange 72 has substantially the same outer diameter as a flange 34 provided along a lower edge of the mouth 33. The airtight plug portion 71 has a recess 73 formed in a sidewall thereof as extending downward from an upper edge thereof. When the rubber plug 7 is in a loose plugging state in which a lower edge of the recess 73 is located below the lower end of the mouth portion 33, an air channel is defined between the rubber plug 7 and the mouth portion 33 by the recess 73. On the other hand, when the rubber plug 7 is in a full plugging state in which the rubber plug 7 is squeezed into the mouth portion 33 in contact with the lower end face of the mouth portion 33, the lower edge of the recess 73 is located inwardly (upwardly) of the lower edge of the mouth portion 33 of the vial, so that the mouth portion 33 is air-tightly sealed. After the drug in the vial is freeze-dried in a freeze-dryer with the rubber plug 7 being in the loose plugging state, the rubber plug 7 having the aforesaid structure can easily be squeezed into the mouth portion 33 of the vial 3 by rubber plug squeezing means equipped in the freeze-dryer thereby to be brought into the full plugging state.

In this embodiment, the lower mouth portion 33 is capped with a cap 8 (rubber plug press) for prevention of inadvertent disengagement of the rubber plug 7 and for improvement of the air-tightness. The cap 8 is engaged with the flange 34 projecting radially outwardly from the lower edge of the mouth portion 33 thereby to be attached to the mouth portion 33. The cap 8 may have the same construction as an annular cap with a lock mechanism disclosed in Japanese Unexamined Patent Publication No. 9-278051 (1997). That is, the cap 8 includes an engagement member 84 having a round top plate 81 and a plurality of engagement tongues 83 provided circumferentially of the top plate 81, and a cylindrical holder member 85 fitted around the plurality of engagement tongues 83 of the engagement member 84. A through-hole 82 for exposing the rubber plug 7 is formed in the center of the top plate 81 of the cap 8. A holder 9 is attached to a lower face of the cap 8, and a cover 10 is removably attached to the holder 9 to close the through-hole 82 until the infusion vessel is used.

The vial 3 is fixedly retained within a cylindrical vial holder 11. The holder 11 is composed of a transparent or translucent resin, and has a flange 11*a* projecting radially outwardly from a lower edge of an outer peripheral surface thereof, and an engagement portion 11*b* provided along a lower edge of an inner peripheral surface thereof for engagement with a lower portion (lower shoulder) of the body of the vial 3. The inner diameter of the holder 11 is matched with the outer diameter of the body 31 of the vial 3. The vial 3 is fixedly fitted in the holder 11.

On the other hand, a cylindrical sleeve 12 is fitted around the holder 11, and attached to the joint 4. Further, the sleeve 12 is fixedly fitted around the proximal portion 41 of the joint 4. The sleeve 12 has a threaded portion 12*a* formed in an inner peripheral surface thereof, while the holder 11 has a threaded portion 11*c* formed in the outer peripheral surface thereof in relation to the threaded portion 12*a*. The holder 11 and the sleeve 12 are threadingly engaged with each other in a relatively rotatable manner for relative axial movement. Therefore, when the holder 11 is rotated in a predefined direction, the vial 3 held in the holder 11 is moved upward together with the holder 11, so that the vial 3 is squeezed toward the joint 4.

In this embodiment, a stopper 13 is removably provided for prevention of the axial movement of the vial 3 with respect to the joint 4. The stopper 13 includes a first restriction portion 13*a* fitted between the upper end face of the upper mouth portion 32 of the vial 3 and the lower surface of the bottom plate 44 of the joint 4 for restricting upward movement (squeeze) of the vial 3, a second restriction portion 13*b* engaged with the holder 11 for preventing the rotation of the holder 11, and a connection portion 13*c* connecting the first and second restriction portions 13*a* and 13*b*. The connection portion 13*c* is fitted around the sleeve 12, and the first restriction portion 13*a* is inserted into the sleeve 12 through an opening 12*b* formed in the sleeve 12. The second restriction portion 13*b* abuts against the lower edge of the sleeve 12, and is engaged with an engagement portion 11*d* (an engagement through-hole in the illustrated embodiment) formed in the holder 11. It is preferred that, after completion of the assembling, the mouth portion is entirely shrink-packaged and the infusion vessel is individually packaged and shipped.

FIGS. 4 to 7 illustrate exemplary assembling processes for the infusion vessel 1 according to the aforesaid embodiment. Where the infusion vessel 1 is assembled through any of these processes, the infusion liquid in the bag 2, the interior surface of the bag 2, the drug in the vial 3, the interior surface of the vial 3, the interior surfaces of the proximal portion 41 and the connector 42 of the joint 4, the projection 47 combining the joint 4 with the intermediate rubber plug 5, a portion adjacent to the opening 46 of the connector 42 of the joint 4, the entire surfaces of the intermediate rubber plug 5, a lower surface of the O-ring 6, the outer peripheral surface and the interior surface of the airtight plug portion 71 of the distal rubber plug 7 and the interior surface of the upper mouth portion 32 of the vial 3 ranging from the portion thereof adjacent to the opening 46 of the connector 42 of the joint 4 to the drug containing portion can all be kept sterile. In the respective process diagrams, steps in a frame denoted by "sterile atmosphere" are performed in a sterile atmosphere, e.g., in a sterile room. The expression "sterilization (EB)" means electron beam sterilization, and the expression "sterilization (EOG)" means ethylene oxide gas sterilization. The expression "EOG/EB" means EOG and/or EB.

When the infusion vessel is to be used, the stopper 13 is removed, and the holder 11 is rotated to squeeze the vial 3 toward the joint 4. When the intermediate rubber plug 5 is disengaged downward from the upper mouth portion 32 of the vial 3 as shown in FIG. 3, the inside space of the bag 2 communicates with the inside space of the vial 3 via the opening 46 of the connector 42, so that the drug in the vial 3 can be mixed with the infusion liquid in the bag 2. At this time, all the portions in contact with the infusion liquid are kept sterile, so that the sterility of the infusion liquid mixture can be ensured.

Then, the cover 10 is removed, and the distal rubber plug 7 is pierced with an instillation needle for instillation of the infusion liquid in which the drug is just dissolved.

According to the present invention, the infusion vessel is capable of easily separately containing the drug and the infusion liquid in a sterile manner and mixing the drug with the infusion liquid in a sterile manner by a simple operation for use, while ensuring the sterility of the connector.

What is claimed is:

1. An infusion vessel comprising:

a vessel body having an inside space serving as an infusion liquid containing portion;

a two-mouth vial having an inside space serving as a drug containing portion;

a joint connecting the vessel body and the vial and guidingly movable relative to the vial;

first and second airtight members attached to the joint;

a third airtight member attached to the vial;

the vessel body having a liquid outlet port provided in a bottom portion thereof;

the vial having upper and lower cylindrical mouth portions provided on vertically opposite sides thereof and having a vertical axis, the lower mouth portion being air-tightly sealed with the third airtight member;

the joint having a proximal portion air-tightly connected to a peripheral edge of the liquid outlet port of the vessel body, and a cylindrical connector extending downward from the proximal portion, the connector having an opening for communication between the inside and the outside thereof;

the first airtight member being attached to the joint below the opening, and fitted in the upper mouth portion of the vial in an axially slidable manner so as to air-tightly close the upper mouth portion of the vial;

the second airtight member being attached to the joint above the opening, and fitted in the upper mouth portion of the vial in an axially slidable manner so as to seal a space defined between the connector and the upper mouth portion of the vial;

wherein the first airtight member is disengaged downward from the upper mouth portion of the vial by moving the vial upward with respect to the joint, so that the inside space of the vessel body communicates with the inside space of the vial via the opening of the connector.

2. An infusion vessel as set forth in claim 1, further comprising a stopper removably provided for prevention of axial movement of the vial with respect to the joint.

3. An infusion vessel as set forth in claim 1, further comprising:

a cylindrical holder for holding the vial; and a sleeve attached to the joint;

wherein the holder and the sleeve are threadingly engaged with each other, so that the vial is axially moved with respect to the joint by moving the holder in threading engagement with the sleeve.

4. An infusion vessel as set forth in claim 1, wherein the vessel body comprises a flexible bag of a resin material, and the joint is composed of a resin material compatible with the resin material for the vessel body.

5. An infusion vessel as set forth in claim 1, wherein the first, second and third airtight members are each composed of a rubber.

6. An infusion vessel as set forth in claim 1, wherein the vial is composed of a glass.

7. An infusion vessel as set forth in claim 1, wherein an infusion liquid in the vessel body, a drug in the vial, interior surfaces of the proximal portion and the connector of the joint, a lower surface of the first airtight member and an interior surface of the upper mouth portion of the vial ranging from a portion thereof adjacent to the opening of the connector of the joint to the drug containing portion are kept sterile.

8. The infusion vessel as set forth in claim 1 wherein the two-mouth vial is movable relative to the vessel body.

9. The infusion vessel as set forth in claim 1 wherein the liquid outlet port communicates between the inside space of the vessel body and the inside space of the two-mouth vial.

10. The infusion vessel as set forth in claim 1 wherein the connector has a central axis and the opening in the connector extends radially through the connector relative to the central axis of the connector.

11. An infusion vessel comprising:

a vessel body having an inside space serving as an infusion liquid containing portion;

a two-mouth vial having an inside space serving as a drug containing portion;

a joint connecting the vessel body and the vial and guidingly movable relative to the vial;

first and second airtight members attached to the joint;

a third airtight member attached to the vial;

the vessel body having a liquid outlet port provided in a bottom portion thereof;

the vial having upper and lower cylindrical mouth portions provided on vertically opposite sides thereof and having a vertical axis, the lower mouth portion being air-tightly sealed with the third airtight member;

the joint having a proximal portion air-tightly connected to a peripheral edge of the liquid outlet port of the vessel body, and a cylindrical connector extending downward from the proximal portion, the connector having an opening for communication between the inside and the outside thereof;

the first airtight member being attached to the joint below the opening, and fitted in the upper mouth portion of the vial in an axially slidable manner so as to air-tightly close the upper mouth portion of the vial;

the second airtight member being attached to the joint above the opening, and fitted in the upper mouth portion of the vial in an axially slidable manner so as to seal a space defined between the connector and the upper mouth portion of the vial;

wherein the first airtight member is disengaged downward from the upper mouth portion of the vial by moving the vial upward with respect to the joint, so that the inside space of the vessel body communicates with the inside space of the vial via the opening of the connector;

a cylindrical holder for holding the vial; and a sleeve attached to the joint;

wherein the holder and the sleeve are threadingly engaged with each other, so that the vial is axially moved with respect to the joint by moving the holder in threading engagement with the sleeve;

wherein the holder is composed of a transparent or translucent resin material.

12. An infusion vessel comprising:

a vessel body having an inside space serving as an infusion liquid containing portion;

a two-mouth vial having an inside space serving as a drug containing portion;

a joint connecting the vessel body and the vial and guidinaly movable relative to the vial;

first and second airtight members attached to the joint;

a third airtight member attached to the vial;

the vessel body having a liquid outlet port provided in a bottom portion thereof;

the vial having upper and lower cylindrical mouth portions provided on vertically opposite sides thereof and having a vertical axis, the lower mouth portion being air-tightly sealed with the third airtight member;

the joint having a proximal portion air-tightly connected to a peripheral edge of the liquid outlet port of the vessel body, and a cylindrical connector extending downward from the proximal portion, the connector having an opening for communication between the inside and the outside thereof;

the first airtight member being attached to the joint below the opening, and fitted in the upper mouth portion of the vial in an axially slidable manner so as to air-tightly close the upper mouth portion of the vial;

the second airtight member being attached to the joint above the opening, and fitted in the upper mouth portion of the vial in an axially slidable manner so as to seal a space defined between the connector and the upper mouth portion of the vial;

wherein the first airtight member is disengaged downward from the upper mouth portion of the vial by moving the vial upward with respect to the joint, so that the inside space of the vessel body communicates with the inside space of the vial via the opening of the connector, wherein the first airtight member is attached to a lower end of the connector of the joint, and has a cross section covering the entire inside space of the upper mouth portion of the vial.

13. An infusion vessel comprising:

a vessel body having an inside space serving as an infusion liquid containing portion;

a two-mouth vial having an inside space serving as a drug containing portion;

a joint connecting the vessel body and the vial and guidinaly movable relative to the vial first and second airtight members attached to the joint;

a third airtight member attached to the vial;

the vessel body having a liquid outlet port provided in a bottom portion thereof;

the vial having upper and lower cylindrical mouth portions provided on vertically opposite sides thereof and having a vertical axis, the lower mouth portion being air-tightly sealed with the third airtight member;

the joint having a proximal portion air-tightly connected to a peripheral edge of the liquid outlet port of the vessel body, and a cylindrical connector extending downward from the proximal portion, the connector having an opening for communication between the inside and the outside thereof;

the first airtight member being attached to the joint below the opening, and fitted in the upper mouth portion of the vial in an axially slidable manner so as to air-tightly close the upper mouth portion of the vial;

the second airtight member being attached to the joint above the opening, and fitted in the upper mouth portion of the vial in an axially slidable manner so as to seal a space defined between the connector and the upper mouth portion of the vial;

wherein the first airtight member is disengaged downward from the upper mouth portion of the vial by moving the vial upward with respect to the joint, so that the inside space of the vessel body communicates with the inside space of the vial via the opening of the connector, said infusion vessel further comprising restriction means for preventing the second airtight member from disengaging downward from the upper mouth portion of the vial.

14. An infusion vessel comprising:

a vessel body having an inside space serving as an infusion liquid containing portion;

a vial having an inside space serving as a drug containing portion and an upper mouth in communication with the inside space of the vial;

a joint connecting the vessel body and the vial and guidingly movable relative to the vial, the joint comprising a cylindrical connector with a central axis, an inside in communication with the inside space of the vessel body, and an opening for communicating infusion liquid in the inside of the cylindrical connector radially through the cylindrical connector; and a first airtight member that is slidable guidingly relative to the vial between a) one position wherein the first airtight member blocks communication of infusion liquid from the inside of the cylindrical connector through the opening in the cylindrical connector into the inside space of the vial and b) another position wherein infusion liquid from inside of the cylindrical connector communicates through the opening in the cylindrical connector into the inside space of the vial.

15. The infusion vessel as set forth in claim 14 wherein the vial has a cylindrical inside surface and the first airtight member is movable guidingly within the cylindrical connector along the central axis.

16. The infusion vessel as set forth in claim 15 wherein the infusion vessel has a vertical axis, the vessel body is above the vial, the first airtight member is below the opening in the cylindrical connector and there is a second airtight member above the opening in the cylindrical connector and acting between the joint and the vial.

17. The infusion vessel as set forth in claim 16 wherein the cylindrical connector and first and second airtight members are movable together along the vertical axis relative to the vial.

* * * * *